(12) United States Patent
Suzuki et al.

(10) Patent No.: US 7,008,594 B2
(45) Date of Patent: Mar. 7, 2006

(54) LUMINESCENT REACTION MEASUREMENT DEVICE

(75) Inventors: Yoshihito Suzuki, Hamamatsu (JP); Akifumi Kamiya, Hamamatsu (JP)

(73) Assignee: Hamamatsu Photonics, K.K., Shizuoka (JP)

( * ) Notice: Subject to any disclaimer, the term of this patent is extended or adjusted under 35 U.S.C. 154(b) by 0 days.

(21) Appl. No.: 10/474,716

(22) PCT Filed: Apr. 11, 2002

(86) PCT No.: PCT/JP02/03626

§ 371 (c)(1),
(2), (4) Date: Jul. 23, 2004

(87) PCT Pub. No.: WO02/086471

PCT Pub. Date: Oct. 31, 2002

(65) Prior Publication Data

US 2004/0241777 A1    Dec. 2, 2004

(30) Foreign Application Priority Data

Apr. 12, 2001    (JP) .............................. 2001-114239

(51) Int. Cl.
    *G01N 21/76* (2006.01)
(52) U.S. Cl. ..................... 422/52; 250/361 C
(58) Field of Classification Search .............. 422/52, 422/82.05, 82.07; 436/172; 250/361 C, 250/207, 214 R
See application file for complete search history.

(56) References Cited

U.S. PATENT DOCUMENTS

| 3,746,513 A | 7/1973 | Warnick et al. |
| 3,882,028 A | 5/1975 | Zolner ........................ 250/361 |
| 3,967,933 A | 7/1976 | Etess et al. .................... 23/232 |
| 4,352,779 A * | 10/1982 | Parks ........................... 422/52 |
| 5,792,621 A * | 8/1998 | Verostko et al. .............. 435/14 |
| 5,847,380 A * | 12/1998 | Tachino et al. ............. 250/207 |
| 5,965,982 A * | 10/1999 | Tachino et al. ............. 313/532 |
| 6,114,621 A * | 9/2000 | Tachino et al. ........... 174/35 R |

FOREIGN PATENT DOCUMENTS

| JP | 53-28233 | 2/1976 |
| JP | 58-226458 | 6/1985 |
| JP | 61-056944 | 3/1986 |
| JP | 63-037243 | 2/1988 |
| JP | 63-37243 | 2/1988 |

(Continued)

*Primary Examiner*—Jeffrey R. Snay
(74) *Attorney, Agent, or Firm*—Morgan, Lewis & Bockius LLP (57) ABSTRACT

Light resulting from chemiluminescence inside a reaction chamber 4 is transmitted through a light transmitting window 3, a large part of the light is made incident on a photoelectric surface 71 of a photomultiplier tube 2 to generate photoelectrons, and these photoelectrons are successively multiplied by surfaces 79 at one side of dynodes 78a, 78, and 78b. Meanwhile, a part of the light that is not made incident on photoelectric surface 71 is made incident on and reflected by a surface 77 at the other side of dynode 78a, returned to reaction chamber 4 via light transmitting window 3, reflected further by light reflecting surfaces 40 and 41 inside reaction chamber 4, emitted again from light transmitting window 3, and made incident on photoelectric surface 71 of photomultiplier tube 2 to generate and multiply photoelectrons in the same manner as the above. The amount of light made incident on photoelectric surface 71 is thus increased by the amount corresponding to the reflection at surface 77 at the other side of the dynode, thereby enabling detection of light caused by weak chemiluminescence.

8 Claims, 5 Drawing Sheets

FOREIGN PATENT DOCUMENTS

| | | |
|---|---|---|
| JP | 04-78546 | 7/1992 |
| JP | 07-333150 | 12/1995 |
| JP | 8-159971 | 6/1996 |
| JP | 08-159971 | 6/1996 |
| JP | 09-005239 | 1/1997 |
| JP | 09-079905 | 3/1997 |
| JP | 9-79905 | 3/1997 |
| JP | 09-089778 | 4/1997 |
| JP | 09-145621 | 6/1997 |
| JP | 09-152405 | 6/1997 |
| JP | 10-83789 | 3/1998 |
| JP | 10-083789 | 3/1998 |
| JP | 11-067145 | 3/1999 |
| JP | 11-67145 | 3/1999 |
| JP | 2002-22662 | 1/2002 |
| WO | WO 02/04931 | 1/2002 |

* cited by examiner

LUMINESCENT REACTION MEASUREMENT DEVICE

TECHNICAL FIELD

This invention concerns a luminescent reaction measurement device, which makes a sample gas react with an oxidizing gas and thereby emits chemiluminescence and detects the light resulting from this luminescence.

BACKGROUND ART

In recent years, there has been an increasing demand for concentration measurement devices of the type, which makes nitrogen monoxide, etc., in a sample gas undergo a chemical reaction with ozone or other oxidizing gas and measures the concentration of the nitrogen monoxide, etc., in the sample gas based on the intensity of the light due to chemiluminescence resulting from the reaction. With such a device, it is possible, for example, to measure the concentration of nitrogen monoxide in the expired air of an asthmatic patient in order to monitor the effects of treatment, and to measure the concentration of nitrogen monoxide in the exhaust gas of an automobile in order to tackle environmental problems.

Such a concentration measurement device requires a luminescent reaction measurement device that measures the intensity of the light due to chemiluminescence, and a luminescent reaction measurement device, such as that disclosed in Japanese Unexamined Patent Publication (Tokukai) No. Hei 7-333150, is popularly used. This device is equipped with a reaction tank, having an indented part formed therein, and a photodiode, having a light receiving surface and serving as a light detector, and this photodiode is fitted into the indented part of the reaction tank so that a reaction chamber of a predetermined space is formed by the light receiving surface and the inner surface of the indented part of the reaction tank.

With this luminescent reaction measurement device, for example, nitrogen monoxide is made to react with ozone in the reaction chamber, the intensity of the light resulting from chemiluminescence is detected by the light receiving surface of the photodiode and an electrical signal according the detection is output.

DISCLOSURE OF THE INVENTION

Improvement of the detection sensitivity of luminescent reaction measurement devices is being desired recently to enable the detection of more dilute gases. However, with the prior-art luminescent reaction measurement device, the light detector forms a part of the wall of the reaction chamber and thus when the light detector is cooled to reduce the noise of the light detector, the temperature of the interior of the reaction chamber drops, thus causing the reaction rate of the chemiluminescence to drop and preventing improvement of the detection sensitivity. Also, if the reaction chamber is made large to increase the amount of light due to chemiluminescence and this is detected by a large light detector, the background noise increases as a result of making the light detector large and furthermore, the heat generated by the light detector itself increases, making the cooling of the light detector difficult and thus preventing improvement of the detection sensitivity.

This invention has been made to resolve the above problems and an object thereof is to provide a luminescent reaction measurement device that can measure light due to chemiluminescence at high sensitivity by a simple arrangement.

This invention provides in a luminescent reaction measurement device, which makes a sample gas and an oxidizing gas react in a reaction chamber and detects, by means of a light detector, the intensity of the light resulting from the chemiluminescence that occurs during the reaction, a luminescent reaction measurement device characterized in that the reaction chamber is arranged with its inner surfaces being light reflecting and is equipped with a light transmitting window that makes the light due to the chemiluminescence in the reaction chamber be emitted towards the light detector that is installed outside the abovementioned reaction chamber, the light detector is a side-on type photomultiplier tube, comprising a cylindrical container, into which the emitted light due to chemiluminescence enters from the peripheral surface, a reflecting type photoelectric surface, photoelectrically converting the light due to chemiluminescence that enters inside the abovementioned container and generating photoelectrons, and a plurality of dynodes, each having, on a surface at one side, a secondary electron emission surface that emits secondary electrons upon incidence of electrons and thereby successively multiplying and outputting photoelectrons, and at least a part of the dynodes receives, on the surface at the other side, the light due to chemiluminescence that enters from the peripheral surface and reflects the light toward the light transmitting window of the reaction chamber.

With this invention's luminescent reaction measurement device, the light resulting from chemiluminescence in the reaction chamber is transmitted through the light transmitting window and a large part of the light is made incident on the photoelectric surface of the photomultiplier tube to cause the generation of photoelectrons, and these photoelectrons are output upon being successively multiplied by the surfaces at one side of the dynodes. Meanwhile, a part of the light is made incident on the surfaces at the other side of the dynodes without being made incident on the photoelectric surface and this light is reflected by the surfaces at the other side of the dynodes, returns to the reaction chamber via the light transmitting window, is reflected furthermore by the light reflecting surface inside the reaction chamber, emitted again from the light transmitting window, made incident on the photoelectric surface of the photomultiplier tube, and photoelectrons are generated, multiplied, and output in like wise manner. The amount of light made incident on the photoelectric surface is thus increased by the amount reflected by the surfaces at the other side of the dynodes to enable the detection of light caused by weak chemiluminescence.

Also, since the photomultiplier tube, which is the light detector, is separated from the reaction chamber and the photomultiplier tube can be cooled to reduce the noise generated in the photomultiplier tube without lowering the temperature of the interior of the reaction chamber, the detection of weaker chemiluminescence is enabled.

Here, the surfaces at the other side of the dynodes that receive and reflect the light due to chemiluminescence are preferably formed of gold.

The surfaces of the other side of the dynodes are thus made high in reflection efficiency and the amount of light returning to the reaction chamber is increased to enable the detection of light caused by weak chemiluminescence to be carried out more favorably.

Also, the dynode that receives and reflects the light due to chemiluminescence by the surface of the other side is preferably a first dynode that first receives the photoelectrons generated by the photoelectric surface. Reflection of light is thereby carried out favorably.

Also, the photomultiplier tube is preferably equipped with a cooling device that cools the photoelectric surface. Cooling of the photoelectric surface is thereby carried out efficiently for reduction of noise and detection of weak chemiluminescence is carried out even more favorably.

BEST MODE FOR CARRYING OUT THE INVENTION

A favorable embodiment of a luminescent reaction measurement device by this invention will be described in detail with reference to the attached drawings. In the description using the drawings, the same or corresponding elements shall be provided with the same symbol and redundant description shall be omitted.

Figure 1:
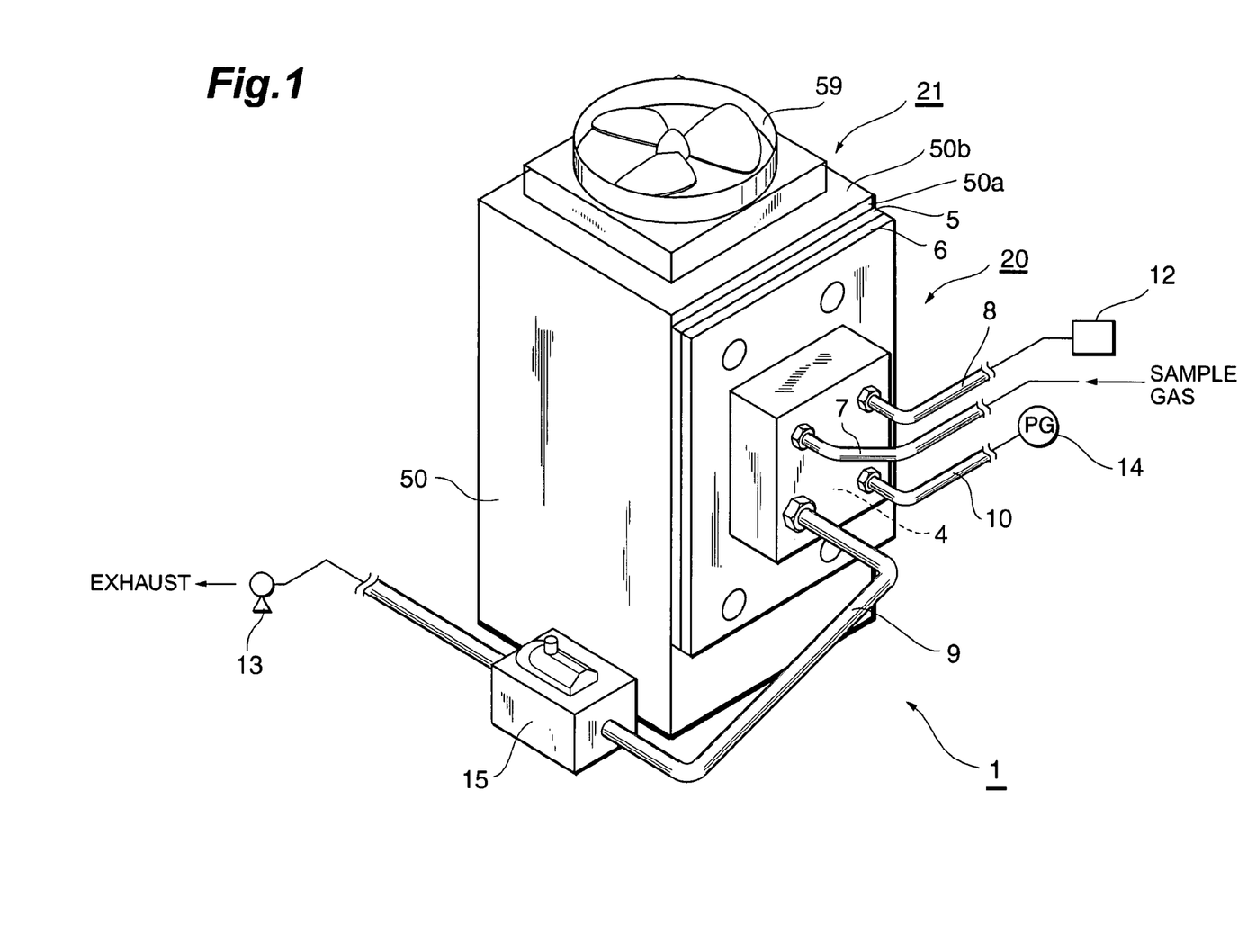
FIG. 1 is a general perspective view showing a luminescent reaction measurement device of an embodiment.

FIG. 1 is a general perspective view showing a luminescent reaction measurement device of an embodiment. Luminescent reaction measurement device 1 of this embodiment measures the concentration of nitrogen monoxide contained in a sample gas, and for this purpose, makes the nitrogen monoxide in the sample gas react with ozone, which serves as an oxidizing gas, to make chemiluminescence occur and measures the intensity of the light resulting from this luminescence.

Luminescent reaction measurement device 1 is equipped with a reaction module 20, which is equipped in turn with a reaction chamber 4 in which the nitrogen monoxide in the sample gas is made to react with ozone, and a light measurement module 21, onto which reaction module 20 is installed and which measures the intensity of the light of the chemiluminescence resulting from the reaction in reaction chamber 4 of reaction module 20.

Figure 2:
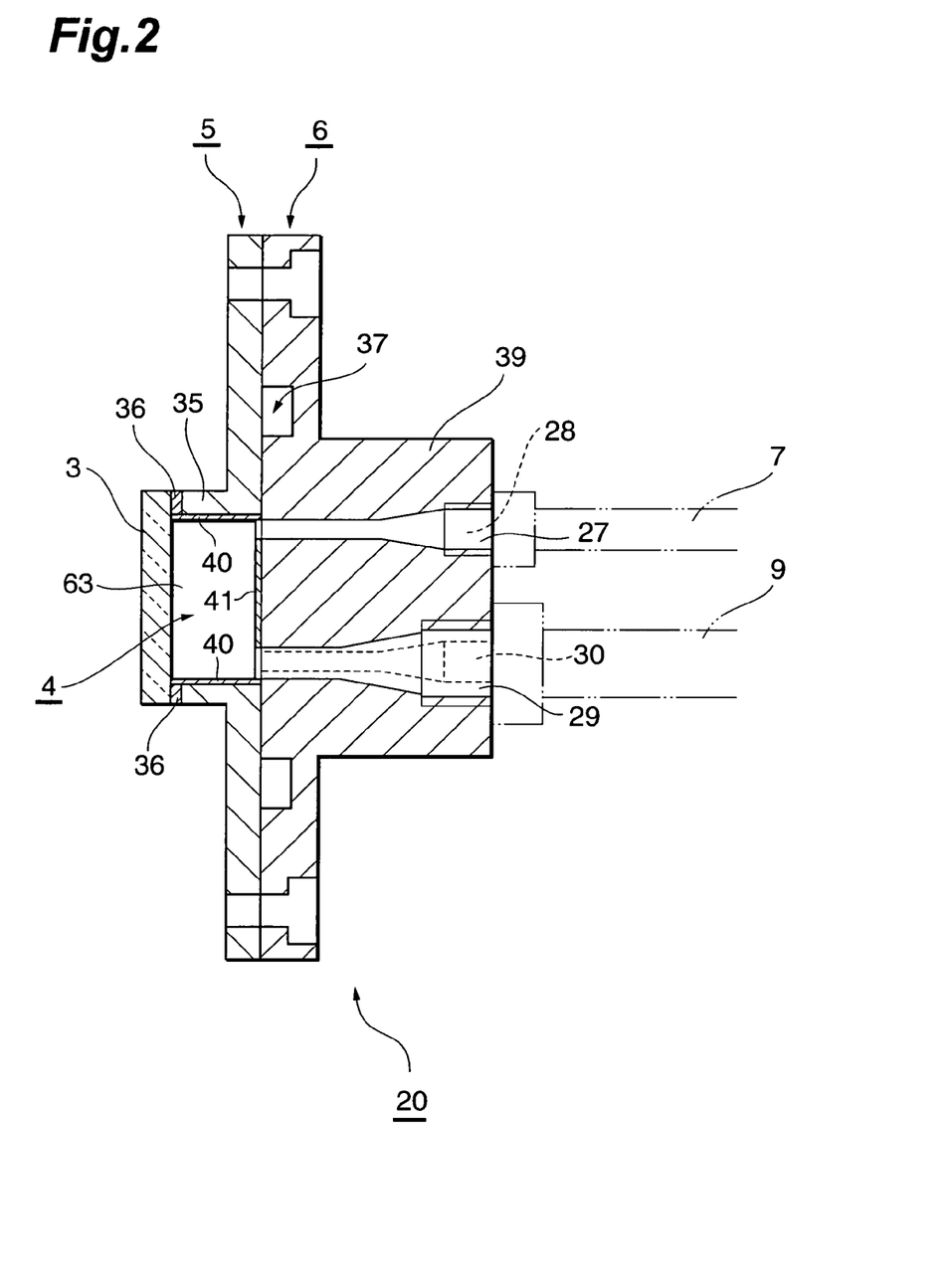
FIG. 2 is a sectional view of the reaction module in FIG. 1.

As shown in FIG. 2, reaction module 20 is equipped with a reaction cell 5, having an indented part 63 formed therein, and a lid plate 6, which serves as a lid for indented part 63 of reaction cell 5 and forms reaction chamber 4 by closing indented part 63.

Reaction cell 5 has an open rectangular tube part 35 formed so as to protrude from a surface at one side (surface at the opposite side of lid plate 6) at the center of a rectangular plate of predetermined thickness. At the end of rectangular tube part 35, a red filter (light transmitting window) 3, having the same outer diameter as rectangular tube part 35 and closing the abovementioned end, is adhered by means of an adhesive agent 36. Indented part 63 is formed by red filter 3 and the inner walls of rectangular tube part 35.

Red filter 3 functions as a long-wavelength transmitting filter that is suitable for the spectrum of the chemiluminescence and emits diffuse light due to the chemiluminescence that occurs inside reaction chamber 4 to the exterior (left side of the figure).

As adhesive agent 36, an adhesive agent, which by itself does not give rise to a gas that causes a luminescent reaction, does not extinguish the luminescent reaction, and is not degraded by the oxidizing gas, etc., is favorable, and for example, a silicon adhesive agent may be used.

On the inner walls of rectangular tube part 35 is formed a gold plating layer 40, which improves the light reflecting property and prevents corrosion due to the oxidizing gas.

Meanwhile, lid plate 6 is a rectangular plate of substantially the same size as reaction cell 5, and at a part that covers indented part 63 of reaction cell 5 and becomes a part of the inner walls of reaction chamber 4, a gold plating layer 41 is formed in the same manner as with the inner walls of rectangular tube part 35 of reaction cell 5. Also at a surface of lid plate 6 that contacts reaction cell 5 at the outer side of reaction chamber 4 a groove 37 for fixing an O-ring is formed in a ring-like manner. Furthermore, at a central part of the rear surface of lid plate 6, a box-like protruding part 39 is formed, and in this protruding part 39 are formed four gas ports 27, 28, 29, and 30, which respectively put the interior of reaction chamber 4 in communication with the exterior.

Figure 3:
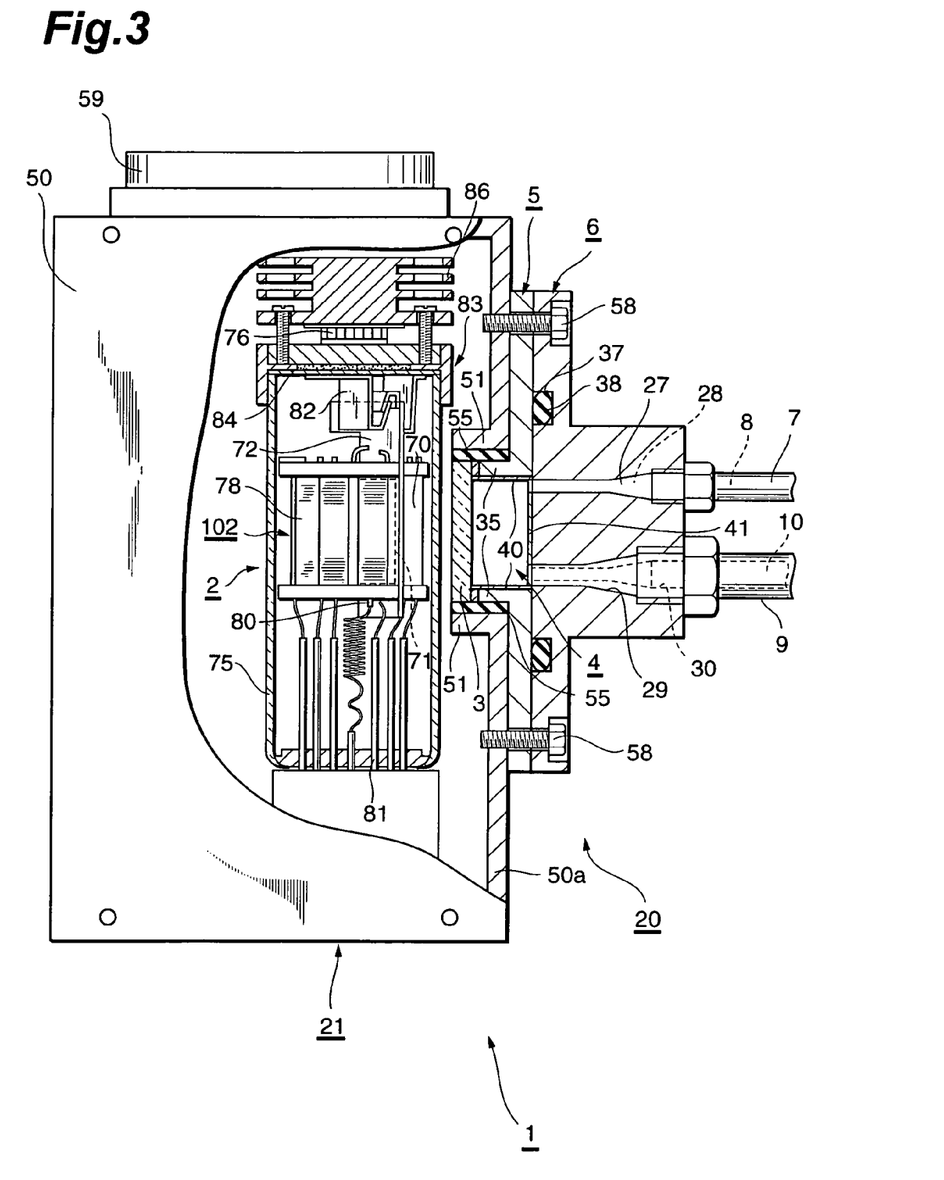
FIG. 3 is a side view partly in section of the luminescent reaction measurement device of FIG. 1.
Figure 4:
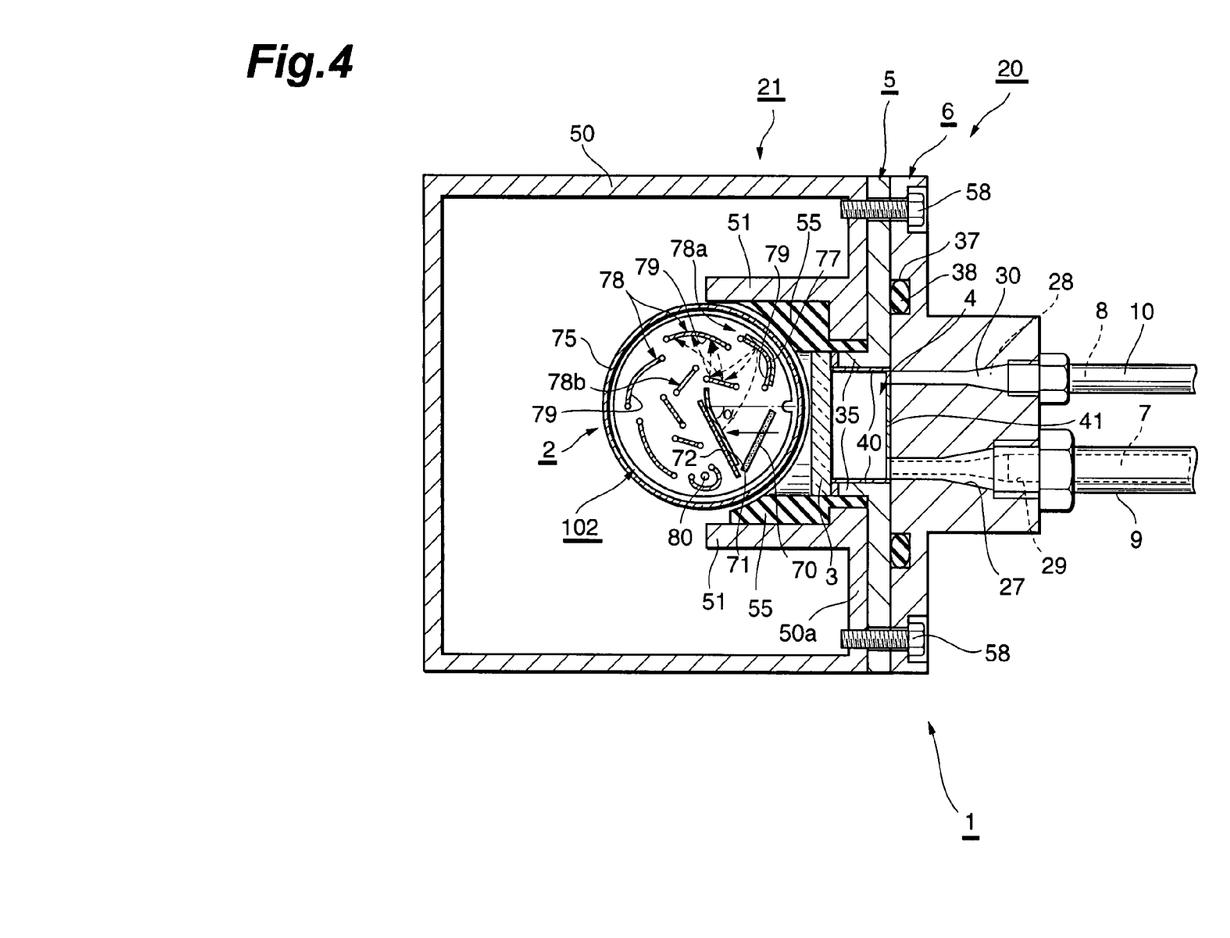
FIG. 4 is a horizontal sectional view of the luminescent reaction measurement device of FIG. 1.

As shown in FIG. 1, light measurement module 21 has a long, box-shaped case 50, and this box-shaped case 50 is equipped with a side plate 50a onto which reaction module 20 is installed. As shown in FIG. 3 and FIG. 4, in the interior of case 50, a photomultiplier tube 2, which detects light due to chemiluminescence from reaction chamber 4 of reaction module 20, is erected close to side plate 50a.

This photomultiplier tube 2 shall now be described in detail. Photomultiplier tube 2 has a cylindrical glass bulb 75 and is equipped with a main detector body 102 inside this glass bulb 75. Main detector body 102 mainly comprises a lattice electrode 70, through which light can be transmitted, a reflecting type photoelectric surface 71, which generates photoelectrons by photoelectric conversion of the light due to chemiluminescence that is made incident upon being transmitted successively through the peripheral surface of glass bulb 75 and lattice electrode 70, a substrate 72, which holds this photoelectric surface 71 on its surface, a plurality of stages of dynodes 78, each having a secondary electron emission surface 79, which emits secondary electrons upon incidence of electrons, formed on a surface at one side and successively multiplying, at this surface at one side, the photoelectrons that are emitted from photoelectric surface 71 and guided by lattice electrode 70, an anode 80, which collects the multiplied photoelectrons and takes them out as an output signal, and a plurality of pin terminals 81 for applying high voltage successively across intervals between lattice electrode 70 and anode 80 as shown in FIG. 3. This photomultiplier tube 2 is a so-called side-on type photomultiplier tube.

As shown in FIG. 4, of the dynodes 78 that comprise this photomultiplier tube 2, a first dynode 78a, onto which the photoelectrons generated at photoelectric surface 71 are made incident first, is curved in a concave manner with respect to photoelectric surface 71, the surface opposing photoelectric surface 71 is made the secondary electron emission surface 79, and the rear surface (surface at the other side) has a gold plating layer (gold) 77 formed thereon.

Also as shown in FIG. 3, with photomultiplier tube 2, a metal conductive plate 84 is installed so as to close the open end at the upper side of glass bulb 75, a setting base 83 of good thermal conductivity is set above conductive plate 84, a Peltier element (cooling device) 76, which cools setting base 83 by the Peltier effect, is installed above setting base 83, and radiating fins 86, which radiate the heat of Peltier element 76, are equipped above Peltier element 76. On the roof plate of case 50 above radiating fins 86 is installed a cooling fan 59, which cools the radiating fins 86. At the lower surface of conductive plate 84 is equipped with a contact piece 82 of good thermal conductivity that connects conductive plate 84 with substrate 72 that holds photoelectric surface 71.

Via substrate 72, contact piece 82, conductive plate 84, and setting base 83, photoelectric surface 71 is cooled efficiently by Peltier element 76, and photoelectric surface 71 is thus maintained adequately at a low temperature so that the generation of noise due to thermions is reduced and the sensitivity is improved. The energy required to cool photoelectric surface 71 is also reduced and the waiting time for cooling is also shortened.

Since photoelectric surface 71 is cooled directly without cooling the entirety of photomultiplier tube 2, the temperature of the interior of reaction chamber 4 is not lowered even if photomultiplier tube 2 and reaction chamber 4 are positioned close to each other, and since photomultiplier tube 2 and reaction chamber 4 can be positioned closer to each other, detection of luminescence at higher sensitivity is enabled.

Also as shown in FIG. 3 and FIG. 4, on side plate 50$a$ of light measurement module 21, a rectangular tube part 51, which protrudes towards the inner side of case 50, is formed at a part opposing main detector body 102 of photomultiplier tube 2 near the center of side plate 50$a$.

On the inner surface of this rectangular tube part 51 is equipped with a rectangular-tube-shaped entry port 55, the inner diameter of which is made the same as the outer diameter of rectangular tube part 35 of reaction cell 5 of reaction module 20, and which guides the light due to chemiluminescence to photomultiplier tube 2, is formed by an insulating material and holds glass bulb 75.

Reaction module 20 is arranged by inserting red filter 3 and rectangular tube part 35 of reaction cell 5 in entry port 55 of light measurement module 21 and overlapping lid plate 6, having an O-ring 38 inserted inside groove 37 for sealing, onto the rear surface of reaction cell 5, and this reaction module 20 is fixed by bolts 58 onto side plate 50$a$ of case 50 of light measurement module 21.

Here, with photomultiplier tube 2, the installation angle in the peripheral direction is set as shown in FIG. 4 so that first dynode 78$a$ does not block the path of light that is made incident on photoelectric surface 71 from reaction chamber 4 and the curving part at the red filter 3 side of gold plating layer 77 on the rear surface of first dynode 78 opposes red filter 3, thereby enabling the light entering from reaction chamber 4 to be received efficiently by photoelectric surface 71 and enabling the light received by a part of the rear surface of first dynode 78$a$ to be reflected efficiently towards red filter 3. The angle $\alpha$ of photoelectric surface 71 with respect to the normal to side plate 50$a$ is preferably set in the range of 61 to 66°, and in this case, photomultiplier tube 2 is positioned so that the line joining the pin of fourth dynode 78$b$ and the center of photomultiplier tube 2 is approximately 90° with respect to the normal to side plate 50$a$.

The inner diameter in the horizontal direction of rectangular tube part 35 of reaction cell 5 (the inner diameter shown in FIG. 4) is set to a wide diameter in order to enable adequate incidence of light from reaction chamber 4 onto photoelectric surface 71 and a part of the rear surface of first dynode 78$a$, and for the same reason, the inner diameter in the vertical direction (the inner diameter shown in FIG. 3) is set greater than or equal to the height of the effective area of photoelectric surface 71 and first dynode 78$a$.

The protruding length (the length shown in FIG. 3 and FIG. 4) of rectangular tube part 35 is set so that in the state in which rectangular tube part 35 is mounted inside entry port 55, the outer surface of red filter 3 is positioned close to glass bulb 75 of photomultiplier tube 2. By thus bringing reaction chamber 4 and photomultiplier tube 2 close to each other, the light due to chemiluminescence, which arises inside reaction chamber 4 and becomes diffuse light, is restrained from attenuating due to diffusion, etc., along the optical path and is made incident efficiently onto photomultiplier tube 2.

Red filter 3 is fixed onto reaction cell 5 using adhesive agent 36, and thus in comparison to a case where red filter 3 is fixed by a bolt and an O-ring, etc., the securing of space, etc., for the strutting of a bolt and for a groove for an O-ring is made unnecessary. Photomultiplier tube 2 and red filter 3 can thus be positioned close to each other and the diffusion of light is restrained to improve the efficiency of convergence and the sensitivity. Experiments by the present inventor have shown that in comparison to cases where red filter 3 is installed using an O-ring and a bolt, etc., without use of adhesive agent 36, luminescent reaction measurement device 1 of the present embodiment is increased by 60% or more in signal amount.

Figure 5:
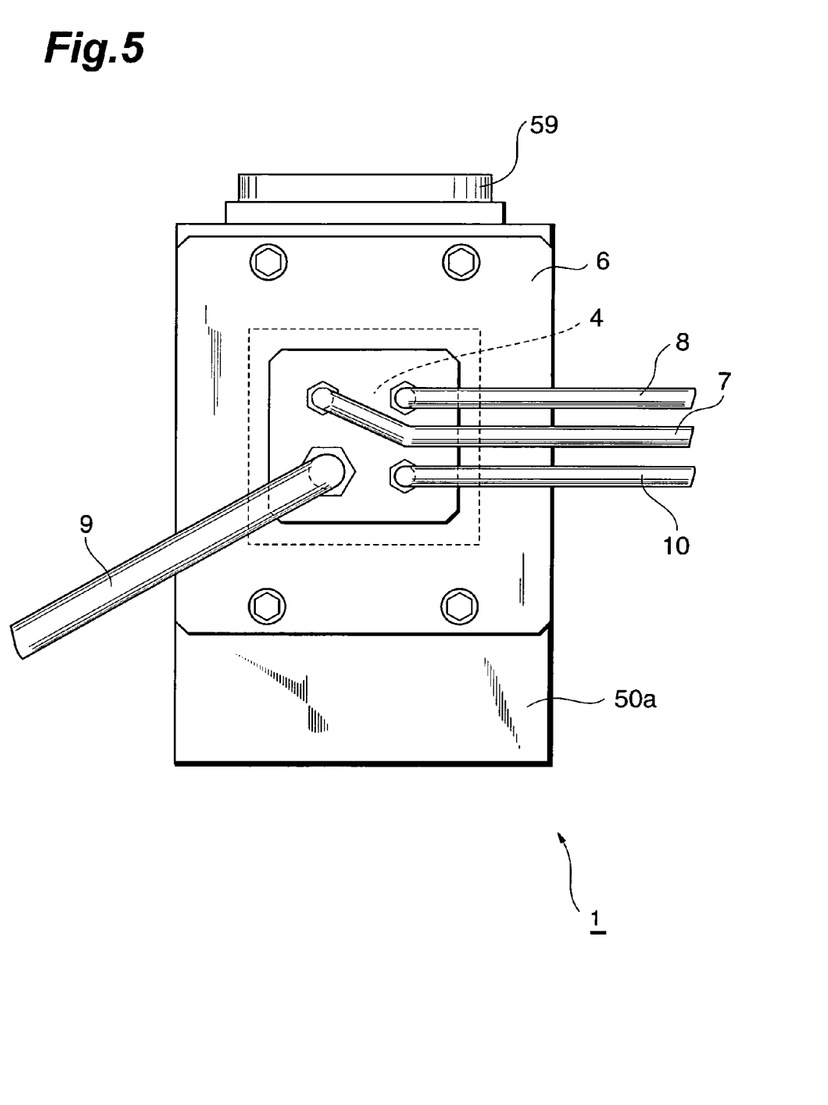
FIG. 5 is a front view of the luminescent reaction measurement device of FIG. 1.

As shown in FIG. 5, gas ports 27 to 30 are connected respectively to a nitrogen monoxide introduction tube 7 for introducing sample gas, containing nitrogen monoxide gas, into reaction chamber 4, an ozone introduction tube 8 for introducing ozone into reaction chamber 4, a gas exhaust tube 9 for exhausting the gas after reaction inside reaction chamber 4, and a pressure measurement tube 10 for detection of the pressure inside reaction chamber 4.

As shown in FIG. 1, ozone introduction tube 8 is connected to an ozone generating device 12, gas exhaust tube 9 is connected via a flow regulating valve 15 to a suction pump 13, and pressure measurement tube 10 is connected to a pressure sensor 14. Since the exhaust gas exhausted from gas exhaust tube 9 may be hazardous to the human body in some cases, it is detoxified by being passed through an activated carbon column, etc., and thereafter released to the atmosphere.

Luminescent reaction measurement device 1 of the present embodiment is arranged as described above. The actions of luminescent reaction measurement device 1 shall now be described. Here, the actions in a case where luminescent reaction measurement device 1 is applied as a device for measuring the concentration of nitrogen monoxide in the expired air of an asthmatic patient shall be described.

First, voltage is applied to main detection body 102 of photomultiplier tube 2 to set up a state in which detection of light is enabled and Peltier element 76 and cooling fan 59 are driven to cool photoelectric surface 71 of photomultiplier tube 2. Ozone from ozone generating device 12 is then introduced via ozone introduction tube 8 into reaction chamber 4 and a patient's expired air that contains nitrogen monoxide is introduced into reaction chamber 4 via nitrogen monoxide introduction tube 7.

At this point, in reaction chamber 4, the nitrogen monoxide in the expired air and the ozone undergo the chemical reaction expressed by the following formula and cause chemiluminescence. Here, $NO_2^*$ indicates nitrogen dioxide in an excited state.

$$NO + O_3 \rightarrow NO_2^* + O_2$$

$$NO_2^* \rightarrow NO_2 + h\nu$$

The light due to this chemiluminescence is then transmitted through red filter 3 and emitted towards photomultiplier tube 2 directly or after being reflected by gold plating layers 40 and 41 on the wall faces of reaction chamber 4. Suction pump 13 is activated to continuously exhaust the gas resulting from this reaction out of the system via gas exhaust tube 9. In this process, flow regulating valve 15 is operated to adjust the exhaust rate so that the amount of light emitted in reaction chamber 4 is maximized.

At this point, a large part of the light that enters photomultiplier tube 2 is made directly incident on photoelectric surface 71. The incident light then undergoes photoelectric conversion at photoelectric surface 71 to become photoelectrons, and these photoelectrons are made incident on the secondary electron emission surface 79 side of the surface of first dynode 78a and multiplied in the form of emission of secondary electrons, which are furthermore multiplied successively by other dynodes 78 and then collected as an output signal at anode 80, thereby providing an output that is in accordance to the luminous intensity.

Meanwhile, the light that is not made directly incident on photoelectric surface 71 is made incident on a part of gold plating layer 77 at the rear surface of first dynode 78a, is reflected by this gold plating layer 77, transmitted through red filter 3, and returned back into reaction chamber 4. The light that is returned inside reaction chamber 4 is then reflected by gold plating layers 40 and 41 of the inner walls inside reaction chamber 4, transmitted through red filter 3, and made incident on photoelectric surface 71 of photomultiplier tube 2, and the generation and multiplication of photoelectrons are carried out to provide an output in the same manner as described above.

The light amount of the light due to chemiluminescence that is made incident on photoelectric surface 71 of photomultiplier tube 2 is thus increased by the amount reflected by part of gold plating layer 77 at the rear surface of first dynode 78a, thereby improving the sensitivity and enabling the detection of light due to weak chemiluminescence.

Also, since photomultiplier tube 2 and reaction chamber 4 are separated and reaction chamber 4 is thus not cooled when photomultiplier tube 2 is cooled so that the luminescent reaction is not inhibited, the light due to a luminescent reaction can be measured at higher sensitivity.

Gold plating layer 77 on the rear surface of first dynode 78a is high in reflection efficiency so that the loss due to reflection of the light that is reflected by first dynode 78a and returns to red filter 3 is low, thus further improving the detection sensitivity.

The data on the intensity of the chemiluminescence light thus obtained by means of photomultiplier tube 2 are analyzed by an external computing device, etc. (not illustrated) to measure the concentration of nitrogen monoxide based on the intensity of chemiluminescence. Here, the intensity of the light due to chemiluminescence is in a proportional relationship with the nitrogen monoxide concentration if the amount of ozone in reaction chamber 4 is adequate, and the nitrogen monoxide concentration can thus be determined by measuring the intensity of the light.

This invention's luminescent reaction device/measurement device is not limited to the embodiment described above.

For example, the luminescent reaction measured with luminescent reaction measurement device 1 is not limited to a reaction of nitrogen monoxide and ozone. For example, besides nitrogen monoxide, ethylene, isoprene, ammonia, or formaldehyde (formalin), etc., which reacts with ozone to give rise to luminescence, may be used as the gas in the sample gas that is subject to concentration measurement. Also, besides ozone, fluorine, chlorine, etc., may be used as the oxidizing gas.

Also, though with the present embodiment, light due to chemiluminescence is reflected by a part of the rear surface of first dynode 78a, this invention is not limited thereto and the light may be reflected by another dynode, such as a ninth dynode.

Also, though with the present embodiment, gold plating layer 77 is formed on the rear surface of first dynode 78a to provide a high light reflecting property, this invention is not limited thereto as long as the reflectance of the light due to chemiluminescence is adequately high, and for example, plating of another noble metal may be used, and depending on the light due to chemiluminescence, the base material of nickel, etc., may be used as it is without plating. The same applies to gold plating layers 40 and 41 of the inner walls inside reaction chamber 4 of reaction module 20, and as long as corrosion resistance is provided and the light reflectance is high, a plating of another metal may be used in the same manner, or a member of solid noble metal, etc., may be mirror polished, etc.

Also, though with the present embodiment, red filter 3 is employed as the light transmitting window, this invention is not limited thereto, and another filter or glass plate, etc., may be used as long as it transmits the light due to chemiluminescence.

Also, though with the present embodiment, Peltier element 76 is equipped as the cooling device and photomultiplier tube 2, in which just photoelectric surface 71 can be cooled efficiently is employed, this invention is not limited thereto, and a side-on type photomultiplier tube and a cooling device that cools the entirety of this photomultiplier tube may be employed, and even in this case, since photomultiplier tube 2 and reaction chamber 4 are separated, reaction chamber 4 will not be cooled and the lowering of the chemiluminescent reaction rate will not occur. Also, in a case where the amount of heat generated by a photomultiplier tube is low, etc., a cooling device does not have to be equipped.

INDUSTRIAL APPLICABILITY

This invention can be applied to the concentration measurement of nitrogen monoxide or other component in a sample gas.

What is claimed is:

1. A luminescent reaction measurement device, which makes a sample gas and an oxidizing gas react in a reaction chamber and detects, by means of a light detector, the intensity of the light resulting from the chemiluminescence that occurs during said reaction, wherein inner surfaces of said reaction chamber are arranged to be light reflecting, and said reaction chamber is equipped with a light transmitting window that makes said light due to chemiluminescence in said reaction chamber be emitted therefrom towards said light detector that is installed outside said reaction chamber, said light detector is a side-on type photomultiplier tube, comprising a cylindrical container, into which emitted light due to chemiluminescence enters through a peripheral surface, a reflecting type photoelectric surface for photoelectrically converting said light due to chemiluminescence that has entered inside said container and generating photoelectrons, and plurality of dynodes, each having, on a surface at one side, a secondary electron emission surface that emits secondary electrons upon incidence of electrons and thereby successively multiplying and outputting said photoelectrons, and at least one of said dynodes receives, on a surface at a second side, said light due to chemiluminescence that has entered through said peripheral surface and reflects it toward said light transmitting window of said reaction chamber.

2. The luminescent reaction measurement device as set forth in claim 1, wherein the surface at the second side of the dynode that receives and reflects said light due to chemilumiescence is formed of gold.

3. The luminescent reaction measurement device as set forth in claim 1, wherein the dynode that receives and reflects said light due to chemiluminescence by the surface of the second side is a first dynode that first receives the photoelectrons generated by said photoelectric surface.

4. The luminescent reaction measurement device as set forth in claim 2, wherein the dynode that receives and reflects said light due to chemiluminescence by the surface of the second side is a first dynode that first receives the photoelectrons generated by said photoelectric surface.

5. The luminescent reaction measurement device as set forth in claim 1, wherein said photomultiplier tube is equipped with a cooling device that cools said photoelectric surface.

6. The luminescent reaction measurement device as set forth in claim 2 wherein said photomultiplier tube is equipped with a cooling device that cools said photoelectric surface.

7. The luminescent reaction measurement device as set forth in claim 3 wherein said photomultiplier tube is equipped with a cooling device that cools said photoelectric surface.

8. The luminescent reaction measurement device as set forth in claim 4 wherein said photomultiplier tube is equipped with a cooling device that cools said photoelectric surface.

* * * * *